United States Patent
Fischer et al.

(10) Patent No.: US 11,970,597 B2
(45) Date of Patent: Apr. 30, 2024

(54) COMPOSITE MATERIAL FOR LOW-WEAR MECHANICAL COMPONENTS FOR FORCE AND MOTION TRANSMISSION

(71) Applicant: FRESENIUS MEDICAL CARE DEUTSCHLAND GMBH, Bad Homburg (DE)

(72) Inventors: Gerome Fischer, Weberstedt (DE); Arne Peters, Bad Homburg (DE); Wolfgang Kunz, Muennerstadt (DE); Scott Cohen, Newton, MA (US)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 517 days.

(21) Appl. No.: 17/056,015

(22) PCT Filed: May 24, 2019

(86) PCT No.: PCT/EP2019/063538
§ 371 (c)(1),
(2) Date: Nov. 17, 2020

(87) PCT Pub. No.: WO2019/224383
PCT Pub. Date: Nov. 28, 2019

(65) Prior Publication Data
US 2021/0198454 A1    Jul. 1, 2021

(30) Foreign Application Priority Data

May 24, 2018   (DE) .................... 10 2018 208 149.2

(51) Int. Cl.
| | | |
|---|---|---|
| C08K 7/14 | (2006.01) | |
| A61M 1/16 | (2006.01) | |
| C08J 5/04 | (2006.01) | |
| C08K 3/04 | (2006.01) | |
| C08K 7/06 | (2006.01) | |
| F04C 2/08 | (2006.01) | |

(52) U.S. Cl.
CPC ............. *C08K 7/14* (2013.01); *C08J 5/042* (2013.01); *C08J 5/043* (2013.01); *C08K 3/04* (2013.01); *C08K 7/06* (2013.01); *F04C 2/08* (2013.01); *A61M 1/1656* (2013.01); *C08J 2371/00* (2013.01); *C08K 2201/003* (2013.01)

(58) Field of Classification Search
CPC ............ F04C 2/08; C08L 71/00; C08L 81/06
See application file for complete search history.

(56) References Cited

U.S. PATENT DOCUMENTS

| | | | |
|---|---|---|---|
| 4,837,251 A | 6/1989 | Okey et al. | |
| 6,231,788 B1 * | 5/2001 | Patel ....................... | C08L 69/00 252/511 |
| 7,575,800 B2 | 8/2009 | Endo et al. | |
| 2016/0010750 A1 * | 1/2016 | Colineau .............. | F16J 15/3232 277/575 |

FOREIGN PATENT DOCUMENTS

| | | | |
|---|---|---|---|
| CN | 102166826 A | 8/2011 | |
| CN | 102558760 B | 10/2014 | |
| DE | 102011076306 A1 * | 11/2012 | ............. B62D 27/00 |
| EP | 3104010 A1 | 12/2016 | |
| JP | S63213560 A | 9/1988 | |
| JP | H06-220322 A | 8/1994 | |
| JP | 2001-295903 A | 10/2001 | |
| JP | 2006226464 A | 8/2006 | |
| WO | 0210320 A1 | 2/2002 | |
| WO | 2015019047 A1 | 2/2015 | |

OTHER PUBLICATIONS

International Preliminary Report on Patentability issued in corresponding International Patent Application No. PCT/EP2019/063538 (English translation) dated Nov. 24, 2020 (7 pages).
International Search Report and Written Opinion issued in corresponding International Patent Application No. PCT/EP2019/063538 (with English translation of International Search Report) dated Sep. 10, 2019 (12 pages).
Examination Report issued in corresponding Indian Patent Application No. 202037048780 dated Jun. 8, 2022 (with English translation) (7 pages).
Sarasua et al., "The mechanical behavior of PEEK short fibre composites," Journal of Materials Science, 1995, vol. 30, pp. 3501-3508.
Office Action issued in Japanese Patent Application No. 2020-564551 dated Jun. 26, 2023 (with English translation of the Office Action)—10 pages total.

* cited by examiner

*Primary Examiner* — Anthony Ayala Delgado
(74) *Attorney, Agent, or Firm* — Kilyk & Bowersox, P.L.L.C.

(57) ABSTRACT

The invention relates to a composite material consisting of at least three constituents, a substrate material, a first fibrous reinforcing material and a second reinforcing material, wherein the first fibrous reinforcing material has a lower thermal expansion coefficient than the second reinforcing material and wherein the second reinforcing material has a lower electrical conductivity than the first reinforcing material, wherein the composite material is provided for use in building components of force and motion transmission, in particular those building components of force and motion transmission which come into contact with ultrapure water.

22 Claims, No Drawings

COMPOSITE MATERIAL FOR LOW-WEAR MECHANICAL COMPONENTS FOR FORCE AND MOTION TRANSMISSION

This application is a National Stage Application of PCT/EP2019/063538, filed May 24, 2019, which claims priority to German Patent Application No. 10 2018 208 149.2, filed May 24, 2018.

FIELD OF THE INVENTION

The invention relates to a composite material for mechanical components which transmit force and motion. The invention further relates to a force and motion-transmitting mechanical component comprising the inventive composite material. The invention further relates to a gear pump having at least one gear comprised of the inventive composite material. The invention likewise relates to the use of the inventive composite material for mechanical components suspended in liquid in medical pumping applications.

BACKGROUND OF THE INVENTION

The present invention relates to the field of composite materials. Composite materials are used for mechanical components which transmit force and motion. Composite materials made from plastics and reinforcing materials are in particular used to lend higher strength, higher wear resistance, less weight and further improved properties to the resulting mechanical components. Force and motion-transmitting mechanical components are used, for example, in gear pumps, in particular in the form of gears.

Gear pumps are used in medical technology, in particular in dialysis machines, to pump therapeutic fluids. This thereby relates to pumps used for pumping fluids as used in dialysis therapy or to degassing pumps for degassing the fluids used in dialysis.

A dialysis machine comprises a hydraulic circuit which substantially ensures the production, conveying and supplying of dialysis fluid. In certain applications, the dialysis fluid is thereby produced in the dialysis machine from provided dialysis concentrates and ultrapure water. The ultrapure water is thereby mixed with the dialysis concentrates in a mixing chamber and transforms into ready-to-use dialysis fluid. Among that which is necessary in producing the dialysis fluid is the degassing and pumping of ultrapure water. These processes are usually realized with gear pumps intended for the purpose. Furthermore, the dialysis machine also comprises pumping apparatus with which the dialysis fluid is pumped to the dialysis filter and made available for extracorporeal hemopurification. In extracorporeal hemopurification, blood drawn from patients is thereby pumped through tubing to the dialysis filter via blood pump apparatus and brought into mass transfer there with the dialysis fluid likewise pumped to the dialysis filter via a semipermeable membrane, thus effecting hemopurification. After such a dialysis treatment is completed, it is hygienically necessary to disinfect the dialysis machine's hydraulic circuit. The hydraulic circuit thereby undergoes a flushing procedure with ultrapure water and disinfectant at increased temperatures of approximately 85° C. Oxidizing agents are in particular used as disinfectants in order to decontaminate the hydraulic circuit.

The gear pumps used in the hydraulic circuit of a dialysis machine are therefore provided to pump dialysis fluids, ultrapure water, oxidizing disinfectants as well as liquid-air mixtures or, respectively, only air for degassing purposes. The greatest pumping activity of these gear pumps is in particular applied to the pumping of dialysis fluids. In addition, it is provided for such gear pumps to also perform pumping procedures under increased temperatures, for example during a heat disinfection of the dialysis machine, e.g. at 85° C. or higher, e.g. up to 90° C. or 95° C.

The gear pumps known and used in the production of dialysis fluids are constructed such that the gears float immersed in the fluid to be pumped during pump operation. The gears are for example thereby mounted in a stainless steel case and can be driven by a rotating magnetic coupling. Gears made of a composite material consisting of a polymer substrate as well as a reinforcing material are usually used for gear pumps in dialysis machines. Gears for gear pumps consisting of a composite material of polyetheretherketone (PEEK) and carbon fibers are known. Using carbon fiber to reinforce PEEK thereby achieves higher strength and lower thermal expansion of the composite material compared to just PEEK alone. It is in particular necessary to reinforce the substrate with the reinforcing material in the case of pumps with floating gears since the gears themselves bear the entire bearing load in this case and are thus subject to very high mechanical stress. Consequently, the composite material requires high mechanical strength in order to be able to build up the desired pressure in the fluid to be pumped on a sustained basis.

For reasons of hygiene, ultrapure water having the highest possible degree of purity is used in the producing of dialysis fluids. Ultrapure water having an electrical conductivity $10^{-4}$ S/m and less is preferably used in producing dialysis fluid. Low electrical conductivity is thereby regarded as the measure for high purity to ultrapure water. However, the high purity of the ultrapure water leads to an adverse effect in respect of gear pumps comprising known composite materials. It has been shown that composite materials containing reinforcing materials of high electrical conductivity such as, for example carbon fibers, exhibit high wear in contact with ultrapure water due to the low electrical conductivity of the ultrapure water. The stability of these gears made from said composite materials in operation is thereby significantly reduced. In particular, contamination of the fluids from abraded particles is thereby also be to reckoned with, which can lead to serious problems during dialysis therapy or the heat cleaning process.

Reinforcing materials of low electrical conductivity based on inorganic materials are known. However, these inorganic materials exhibit comparatively high thermal expansion. High thermal expansion likewise leads to increased wear in mechanical components of force and motion transmission. Corresponding composite materials of a polymer substrate and an inorganic reinforcing material are hence likewise unsuitable for applications at increased temperatures. In particular, gears in gear pumps of dialysis machines made from such a composite material would not endure the heat cleaning operation without high material wear.

WO 2015/019047 A1 discloses building components made of a first part and a second part, wherein the first part comprises a first semi-crystalline polymer with phenylene, carbonyl and ether moieties. The second part comprises a second semi-crystalline polymer likewise having phenylene, carbonyl and ether moieties. The second polymer thereby has a melting temperature which is lower than the melting temperature of the first polymer. In one realization, a first and second polymer can be part of a first and second composite comprising a filler, e.g. either glass fiber or carbon fiber. In a further realization, WO 2015/019047 A1 describes a gear consisting of two parts, wherein the second part defines a support, and the first part comprises the teeth of the gear. The second part is thereby reinforced by a fibrous material, e.g. in the form of a fabric.

U.S. Pat. No. 4,837,251 describes a composition for a pressure-formed core of a composite structure. The composition contains a thermoplastic resin selected from among the group of polyether ether ketone, polyether ketone, polyaryl sulfide, polyaryl ketone, polyaryl sulfone or polyaryl ether sulfone. In one realization, the composition comprises carbon fibers, glass fibers and glass microspheres.

WO 02/10320 discloses plastic compositions for producing plastic bearings. In one realization, the plastic composition consists of a polymeric matrix material selected from among the group comprising polyamide imide, polyether imide, polyimide, polyether ether ketone, polyphenylene sulfide, a liquid crystal polymer or mixtures thereof. The plastic composition according to this realization further contains carbon fibers and an additive selected from among the group comprising boron nitride, carbon, graphite, molybdenum disulfide, talc, tetrafluoroethylene and combinations thereof.

The composite materials disclosed in the prior art present no satisfying solution for the formulated problems. In particular, the prior art discloses no composite materials of low thermal expansion and thus advantageous wear characteristics making them suitable for mechanical components of force and motion transmission.

OBJECT OF THE INVENTION

In a first aspect of the invention, it was therefore an object to provide a composite material for mechanical components of force and motion transmission which surmounts the aforesaid disadvantages of high wear when in contact with ultrapure water and of high wear caused by thermal expansion.

In a further aspect of the invention, it was therefore an object to provide a mechanical component for transmitting force and motion, in particular a gear, having improved wear characteristics when in contact with ultrapure water and under increased temperature applications.

In a further aspect of the invention, it was therefore an object to provide a gear pump for pump applications employing ultrapure water and higher temperatures which exhibits improved wear characteristics and thus a longer life and less susceptibility to malfunction.

SUMMARY OF THE INVENTION

In a first aspect of the invention, the object is solved by a composite material for mechanical components of force and motion transmission as described herein.

In a second aspect of the invention, the object is solved by a mechanical component for transmitting force and motion as described herein.

In a third aspect of the invention, the object is solved by a gear pump as described herein.

In a fourth aspect of the invention, the object is solved by the use of a composite material as described herein for mechanical components suspended in liquid in medical pumping applications.

DETAILED DESCRIPTION OF THE INVENTION

In a first aspect, the invention relates to a composite material for mechanical force and motion-transmitting building components consisting of at least three constituents:

(i) at least 45% by weight of a substrate material in relation to the total weight of the composite material,
(ii) 3 to 20% by weight of a first fibrous reinforcing material in relation to the total weight of the composite material, and
(iii) 10 to 45% by weight of a second reinforcing material in relation to the total weight of the composite material, whereby the first fibrous reinforcing material has a lower thermal expansion coefficient than the second reinforcing material and wherein the second reinforcing material has a lower electrical conductivity than the first reinforcing material and wherein the parts by weight of the constituents contained in the composite material add up to 100%.

As apparent from the above, the composite material of the present invention may contain, in addition to the three constituents mentioned, further constituents which can be freely selected according to respective embodiments and requirements. In any case, parts of the present constituents add up to 100% by weight.

In a further embodiment according to the first aspect, the composite material is characterized by the first fibrous reinforcing material exhibiting a thermal expansion of from $-0.15 \times 10^{-6}$/K to $2 \times 10^{-6}$/K parallel to the direction of the fibers and the second reinforcing material having an electrical conductivity of $10^{-4}$ S/m or less.

Compared to known prior art composite materials only having one reinforcing material with high electrical conductivity and low thermal expansion such as e.g. carbon fiber, the composite material is characterized by clearly reduced wear. Additionally, the composite material has such a low thermal expansion coefficient that the composite material is also suited to the production of mechanical components for the transmission of force and motion at increased temperatures. Furthermore, the inventive composite material is characterized by a low coefficient of friction. Furthermore, compared to known prior art composite materials only having a reinforcing material of low electrical conductivity but high thermal expansion such as e.g. glass fiber, the inventive composite materials are characterized by clearly reduced wear. It was moreover determined that the composite material also exhibits high resistance to oxidative effects.

The thermal expansion of reinforcing materials is determined by known methods of thermomechanical analysis (TMA) in the technically relevant temperature range of 10 to 110° C. The DIN 51045-1:2005-8 standard is particularly known for determining thermally induced length changes in solids. Thermal expansion and electrical conductivity of reinforcing materials is moreover documented in the technical literature.

As defined by the present application, the term "composite material" is to be understood as a cohesive mass of different materials differing in terms of their material properties. The materials thereby differ in mechanical properties such as, for example, tensile strength, thermal properties such as e.g. thermal expansion, melting temperature or glass transition temperature, or in chemical properties. In particular to be understood by the term "composite material" in the sense of the present invention is a compound of substrate and reinforcing materials. "Substrate" thereby refers to a material which demonstrates a continuous phase in the composite material. In accordance with the present invention, a polymer is used as the substrate material. Preferentially, polymers in the sense of the present invention exhibit a high melting temperature and/or high glass transition temperature such that they also remain dimensionally stable at increased temperatures. In addition, however, these polymers are characterized by temperature-sensitive softening characteristics such that the polymers can be processed above their melting temperature in the melted state.

As defined by the present application, the term "reinforcing material" is to be understood as a material which exhibits higher tensile strength and/or wear resistance compared to the substrate. In particular, the reinforcing material in combination with the substrate lends the composite material higher tensile strength. In accordance with the present invention, at least two reinforcing materials are provided. Reinforcing materials can be fibrous or non-fibrous, e.g. particulate or plate-like matter. Known fibrous reinforcing materials are, for example, glass fiber, carbon fiber, asbestos fiber, silica fiber, alumina fiber, zirconium oxide fiber, boron nitrite fiber or silicone nitrite fiber. Known non-fibrous reinforcing materials are, for example, mica, silica, talc, alumina, kaolin, calcium sulfate, calcium carbonate, titanium dioxide, ferrite, clay, glass powder, zinc oxide, ferric oxide, powdered silica, magnesium carbonate, graphite, carbon powder, e.g. also in the form of nanotubes.

The composite material according to the present application consisting of at least three constituents is preferably produced in a compounding process. The polymeric substrate is thereby mixed with the first fibrous reinforcing material and the second reinforcing material at an increased temperature which is preferably higher than the melting temperature of the polymeric substrate. The increased temperature is thereby lower than the decomposition temperature of the polymeric substrate. In the sense of the present application, the "melting temperature" of the polymeric substrate is to be understood as the melting temperature determined as per differential scanning calorimetery (DSC) methods. The DIN EN ISO 11357-3:2013-04 standard is particularly known in determining the melting temperature of plastics. Advantageously, the melted polymeric substrate can slightly coat the reinforcing materials such that the first fibrous reinforcing material and the second reinforcing material are evenly distributed and encapsulated in the polymeric substrate.

The polymeric substrate and the first fibrous reinforcing material and second reinforcing material can be supplied continuously at one point of the compounding process at which they are mixed, heated and formed into the composite material by extrusion. In one example, a mass of the fibrous reinforcing material can be passed through a melt of the polymeric substrate. The mass can comprise a continuous length of fibrous filler or, more preferentially, a plurality of continuous filaments consolidated at least to a certain extent. The continuous fibrous mass can for example comprise a mesh, netting or fibrous web. The filaments, of which the fibrous mass consists, can be distributed substantially evenly or stochastically within the mass and additionally oriented as applicable without preferred direction.

Alternatively, the composite material can be produced in a process in which a predetermined quantity of the first polymeric substrate and a predetermined quantity of the first fibrous reinforcing material and the second reinforcing material are to be obtained in the melt by mixing.

Preferentially provided is for the first fibrous reinforcing material and the second reinforcing material to be isotropically dispersed in the substrate by the selected production method. This means that the distribution of the first reinforcing material and the second reinforcing material in the substrate is not position-dependent and the orientation of the fibers does not exhibit a preferred direction. The material properties of the composite material are thus not dependent on a potential orientation of the first fibrous reinforcing material and the second reinforcing material in the substrate. The mechanical properties of the composite material and the mechanical force and motion-transmitting building components produced from the composite material are therefore the same in all orientations, which represents an advantage.

The first fibrous reinforcing material preferably exhibits a thermal expansion coefficient of $-0.15 \times 10^{-6}$/K to $2 \times 10^{-6}$/K parallel to the direction of the fibers. The thermal expansion coefficient value of the first fibrous reinforcing material is very low or respectively negative compared to the polymeric substrate. Typical thermal expansion coefficients of suitable polymeric substrates in the sense of the present invention lie in a range between $30 \times 10^{-6}$/K and $60 \times 10^{-6}$/K. Fibrous reinforcing materials having a negative thermal expansion coefficient are preferential since they counteract the naturally high total thermal expansion of the polymeric substrate to a certain degree and are responsible for an overall low thermal expansion of the composite material. An isotropic distribution of the first fibrous reinforcing material in the polymeric substrate thereby results in a consistent compensating of the substrate's thermal expansion in all spatial directions. In preferential embodiments, the first fibrous reinforcing material exhibits a thermal expansion coefficient of $-0.12 \times 10^{-6}$/K or more, in particular $-0.1 \times 10^{-6}$/K or more, in particular $-0.8 \times 10^{-6}$/K or more, in particular $0.5 \times 10^{-6}$/K or more, in particular $-0.02 \times 10^{-6}$/K or more, but less than $1.8 \times 10^{-6}$/K, in particular less than $1.5 \times 10^{-6}$/K, in particular less than $1.2 \times 10^{-6}$/K, in particular less than $1 \times 10^{-6}$/K, in particular less than $0.8 \times 10^{-6}$/K, in particular less than $0.5 \times 10^{-6}$/K.

According to the invention, the second reinforcing material exhibits an electrical conductivity amounting to $10^{-4}$ S/m or less. The low conductivity of the second reinforcing material effects a reduced susceptibility to composite material wear. It was surprisingly determined that the specific rate of wear of the inventive composite material is unexpectedly lower than that of the substrate alone or that of the composite material consisting solely of the polymeric substrate and the first fibrous reinforcing material or that of the composite material consisting solely of the polymeric substrate and the second reinforcing material. In preferential embodiments, the electrical conductivity of the second reinforcing material is $10^{-5}$ S/m or less, in particular $10^{-6}$ S/m or less, in particular $10^{-7}$ S/m or less, in particular $10^{-8}$ or less, in particular $10^{-9}$ S/m or less, in particular $10^{-10}$ S/m or less, however at least more than $10^{-15}$ S/m, in particular more than $10^{-14}$ S/m, in particular more than $10^{-13}$ S/m, in particular more than $10^{-12}$ S/m, in particular more than $10^{-11}$ S/m.

In a further embodiment according to the first aspect, the invention is characterized by the second reinforcing material being fibrous. Fibrous reinforcing materials are preferential since they lend the substrate a higher stability, in particular a higher tensile strength and a higher impact strength. Depending on the required stability of the composite material and the intended loading as a mechanical component for transmitting force and motion, the use of the second reinforcing material in fiber form can thereby be advantageous.

In a further embodiment according to the first aspect, the invention is characterized by the polymeric substrate exhibiting a glass transition temperature of from 120 to 200° C., preferentially 125° C. to 190° C., further preferentially 130° C. to 160° C. Glass transition temperatures can for example be determined per differential scanning calorimetry (DSC) methods. The DIN EN ISO 11357-2:2014-07 standard is particularly known for determining glass transition temperature. Above the glass transition temperature, the thermally induced softening of the polymeric substrate increases with increasing temperature, in particular under mechanical load. The glass transition temperature is therefore to be regarded as a measure of the thermal softening characteristics of polymers. In the sense of the present invention, particularly polymers having a glass transition temperature of 120° C. and higher are to be regarded as hard and thus preferentially suitable as polymeric substrates for a composite material according to the present invention.

In a further embodiment according to the first aspect, the invention is characterized by the polymeric substrate having a coefficient of friction of from 0.13 to 0.21 μs and/or a specific rate of wear of 2 to 6×10$^{-6}$ mm$^3$/Nm as measured by the "Block on the Ring Test." The "Block on the Ring Test" employed for the testing is based on the description of the ASTM G77-17 standard. The workpiece to be examined is thereby put under load on a metal ring and the ring is set into rotation. The coefficient of friction and the specific wear rate are determined subject to this experimental arrangement. Using a polymeric substrate with a coefficient of friction from 0.13 to 0.21 μs and/or a specific rate of wear of 2 to 6×10$^{-6}$ mm$^3$/Nm is advantageous in the producing of the composite material together with the first fibrous reinforcing material and the second reinforcing material as regards the overall regulating of the composite material's advantageous low frictional coefficient and specific wear rate values.

In a further embodiment according to the first aspect, the invention is characterized by the polymeric substrate being a polymer selected from among the group consisting of polyaryl ether ketones and polyaryl sulfones, preferentially a polymer selected from among the group consisting of polyether ether ketones (PEEK), polyether ketones (PEK), polyetherketone ketones (PEKK), polyetherketone etherketone ketones, polyphenylene sulfides (PPS), polyphenylene sulfones (PPSU), polysulfones (PSU), polyether sulfones (PESU) or mixtures thereof. Further preferentially, the polymeric substrate is a polyether ether ketone (PEEK). In terms of their temperature resistance, their mechanical properties, their chemical inertness and their processability when molten, these polymers are particularly suitable for producing the inventive composite materials.

In a further embodiment according to the first aspect, the invention is characterized by the first fibrous reinforcing material being carbon fibers. In the sense of the invention, the term "carbon fiber" is to be understood as fiber obtained from a plastic fiber in a pyrolysis process. Carbon fibers are characterized by high tensile strength and by low, in particular negative, thermal expansion coefficients parallel to the direction of the fibers. The isotropic arrangement to the carbon fibers in the inventive composite material can thereby keep the temperature-sensitive expansion of the composite material, and thus the wear of force and motion-transmitting mechanical components made from the composite material, low.

In a further embodiment according to the first aspect, the invention is characterized by the second reinforcing material being glass fibers. Glass fibers are characterized by high tensile strength and thereby lend the composite material an increased elongation at break. Glass is further characterized by low electrical conductivity. The wear of force and motion-transmitting mechanical components made from the composite material and which come into contact with ultrapure water is thereby reduced.

In a further embodiment according to the first aspect, the invention is characterized by the percentage of the first fibrous reinforcing material in the composite material relative to the total weight of the composite material amounting to 3% by weight or more, preferentially 4% by weight or more, further preferentially 5% by weight or more, further preferentially 6% by weight or more, further preferentially 7% by weight or more, and 20% by weight or less, preferentially 19% by weight or less, further preferentially 18% by weight or less, further preferentially 17% by weight or less, further preferentially 16% by weight or less, further preferentially 15% by weight or less, in particular 3% to 18% by weight, further preferentially 5% to 18% by weight, further preferentially 5% to 15% by weight, further preferentially 7% to 15% by weight. A too high percentage of more than 20% by weight of the first fibrous reinforcing material, e.g. carbon fiber, relative to the total weight of the composite material results in unacceptably high wear when same is used for force and motion-transmitting mechanical components coming into contact with ultrapure water. When the percentage of the first fibrous reinforcing material, e.g. carbon fiber, is less than 3% by weight relative to the total weight of the composite material, the high thermal expansion of the polymeric substrate or the second reinforcing material, e.g. glass fiber, can no longer be sufficiently compensated. Correspondingly, at increased temperatures, the mechanical component can wear due to excessively high thermal expansion in applications of force or motion transmission.

In a further embodiment according to the first aspect, the invention is characterized by the percentage of the second reinforcing material, e.g. glass fiber, in the composite material relative to the total weight of the composite material amounting to 10% by weight or more, preferentially 12% by weight or more, preferentially 14% by weight or more, further preferentially 15% by weight or more, further preferentially 17% by weight or more and no more than 45% by weight, preferentially no more than 42% by weight, further preferentially no more than 40% by weight, further preferentially no more than 38% by weight, further preferentially no more than 35% by weight, further preferentially no more than 33% by weight, further preferentially no more than 30% by weight, particularly preferentially 10% to 40% by weight, further preferentially 15% to 35% by weight, further preferentially 15% to 30% by weight.

A percentage of the second reinforcing material, e.g. glass fiber, of more than 45% by weight relative to the total weight of the composite material can cause a thermal expansion of the composite material which is too high, which at increased temperatures in particular results in unacceptable wear of force and motion-transmitting mechanical components produced from the inventive composite material. A too-low percentage of the second reinforcing material, e.g. glass fiber, of less than 10% by weight relative to the total weight of the composite material needs to be compensated by a further reinforcing material, e.g. the first fibrous reinforcing material, so that the composite material will have sufficient stability for force and motion-transmitting mechanical components. Since these reinforcing materials are not inert to ultrapure water due to the higher electrical conductivity, unacceptable wear would be expected when such mechanical components are used in contact with ultrapure water.

In a further embodiment according to the first aspect, the invention is characterized by the percentage of the polymeric substrate in the composite material amounting to 45% by weight or more, preferentially 50% by weight or more, further preferentially 55% by weight or more, further preferentially 60% by weight or more relative to the total weight of the composite material. A percentage of polymeric substrate of less than 45% by weight can lead to the first fibrous reinforcing material and the second reinforcing material not being completely encapsulated by the polymeric substrate. This can thereby lower the stability of the composite material and can lead to increased wear when the composite material is used for force and motion-transmitting building mechanical components.

In a further embodiment according to the first aspect, the invention is characterized in that the composite material contains an antioxidant. The antioxidant prevents degradation of the substrate material and the first fibrous reinforcing material in the composite material caused by ion or radical formation.

In particular, charges are induced on composite materials used in building components for the transmission of force and motion by frictional contact and the resulting triboelectric effect. In case of the composite material being defined according to the first aspect, the electric charges are induced by homolytic and heterolytic covalent bond cleavage in the substrate material and/or the first fibrous reinforcing material, i.e. in particular the carbon fiber material.

The heterolytic bond cleavage generates a pair of ions by cleaving covalent bonds, whereby the ionic sites are located at the molecular cleavage fragments of the substrate material or the fibrous reinforcing material. Within the meaning of the present application, the ionic sites generated in this way in the substrate material or in the first fibrous reinforcing material are referred to as mechano-ions because they are generated by mechanical frictional contact. The mechano-ions comprise cationic mechano-ions, i.e. positively charged molecular cleavage fragments, and anionic mechano-ions, i.e. negatively charged molecular cleavage fragments.

Homolytic bond cleavage produces a pair of radicals, wherein the radical sites are located at the respective molecular cleavage fragments. Within the meaning of the present application, such radical sites are called mechano-radicals because they are generated by mechanical frictional contact.

Mechano-ions and mechano-radicals cause subsequent chemical reactions, which in turn cause new covalent bond cleavage and thus contribute to degradation and loss of strength of the composite material. If the formation of such machano ions and machano radicals is counteracted, weakening of the composite material can be avoided. Ultrapure water with a conductivity of $10^{-4}$ S/m is not suitable for reacting with mechano-ions and mechano-radicals in sufficient quantities, since it contains only a few ions that can react with the mechano-ions or mechano-radicals in the composite material. Therefore, it turns out to be a problem that composite materials, according to the first aspect of the invention, lose their strength when used as a force- or motion-transmitting building component and in combination with ultrapure water when exposed to excessive frictional stress due to the tribological effect.

Under conditions of high frictional stress and in contact with ultrapure water, the strength of the composite materials according to the first aspect of the invention can be further increased by a proportion of antioxidant in the composite material.

The production of a composite material containing antioxidants can be carried out by melt extrusion and compounding the constituents of the substrate material, the first fibrous reinforcing material, the second reinforcing material and antioxidants to form the composite material. Within the present application, the term 'antioxidant' shall mean one or more substances that are chemically reactive with respect to ions or radicals. According to the present application, the antioxidants used are those which are reactive with mechano-ions and mechano-radicals formed in the composite material according to the first aspect of the invention.

In particular, compounds such as tocopherols, tocotrienols, resveratroles, flavonoids, H-donors such as aromatic amines and sterically hindered phenols, hydroperoxide decomposers such as phosphites, phosphonites, thiosynergists, alkyl radical scavengers such as e.g. sterically hindered amine stabilizers, hydroxylamines, benzofuranones, acryloyl-modified phenols, or multifunctional stabilizers of the aforementioned type, or mixtures of stabilizers of the aforementioned type may be used.

In a further embodiment according to the first aspect, the invention is characterized in that the antioxidant is a primary and/or a secondary antioxidant. The primary antioxidant can be sterically hindered phenols or secondary aromatic amines. The term "steric" refers to spatially demanding molecular groups at the molecular level. A preferred primary antioxidant is the commercially available Evernox 1330, which contains the compound 3,3',3',5,5',5'-hexa-tert-butyl-a,a',a'-(mesitylene-2,4,6trityl)tri-p-cresol. The secondary antioxidants may be peroxides, organic hydroperoxides, phophites, thioethers or organic sulfides. A preferred secondary antioxidant is the commercially available Doverphos S-9228, which contains the compound bis(2,4-dicumylphenyl) pentaerythritol diphosphite. The use of primary antioxidants is preferred.

In a further embodiment according to the first aspect, the invention is characterized in that the proportion of the antioxidant in the composite material is 0.001% to 2.5% by weight, preferably 0.01% to 2.0% by weight, more preferably 0.1% to 1% by weight, based on the total weight of the composite material. In particular, the proportion of the antioxidant in the specified range has only an insignificant effect on the material properties of the composite material with regard to electrical conductivity and thermal expansion, so that wear of the composite material in its use as a mechanical component in the transmission of force and movement in the case of ultrapure water contact and thermal expansion does not occur.

In particular the present composite material according to the first aspect of the invention may be further characterized in that the proportions of the substrate material, the first fibrous reinforcing material and the second reinforcing material and the antioxidant together result to 100% by weight.

In a further embodiment according to the first aspect, the invention is characterized by the weight ratio of the second reinforcing material to the fibrous first reinforcing material in the composite material amounting to 3:1 to 1:1. It has been shown that the wear rate of the composite material in force and motion-transmitting mechanical components exhibits the lowest values when this weight ratio range is used.

In a further embodiment according to the first aspect, the invention is characterized by the fibers of the fibrous first reinforcing material and/or the fibers of the fibrous second reinforcing material having a fiber diameter across the longitudinal extension of the fibers of 1 μm or more, preferentially 2 μm or more, further preferentially 3 μm or more and 10 μm or less, further preferentially 9 μm or less, further preferentially 8 μm or less, in particular 1 μm to 10 μm, preferentially 2 μm to 9 μm, further preferentially 3 to 8 μm.

In a further embodiment according to the first aspect, the invention is characterized by the fibers of the fibrous first reinforcing material and/or the fibers of the fibrous second reinforcing material having a length of 10 μm or more, preferentially 15 µm or more, preferentially 20 µm or more, preferentially 25 µm or more and 60 µm or less, preferentially 55 µm or less, further preferentially 50 µm or less, in particular from 10 µm to 60 µm, preferentially from 15 µm to 55 µm, further preferentially from 20 µm to 50 µm. Fiber lengths greater than 60 µm can prevent an advantageous isotropic distribution of the fibers in the composite material. Particularly in the case of small mechanical components, a fiber length greater than 60 µm can lead during manufacture of the building component to a fiber orientation which can negatively affect building component stability. Lesser fiber lengths of 10 µm or less can result in the fibrous first or second reinforcing material losing their cross-linking character in the composite material and result in reduced composite material stability.

In particular, a preferential range of fiber diameter and length for the first fibrous and the second fibrous reinforcing material is to be selected such that a ratio of diameter to length for the fibers of the first fibrous reinforcing material and the fibers of the second fibrous reinforcing material amounts to 1:2 to 1:20. At least 60%, preferentially at least 70%, further preferentially at least 80% of the fibers of the first fibrous and the second fibrous reinforcing material are thereby at this preferential ratio.

In a further embodiment according to the first aspect, the invention is characterized by the composite material comprising a further constituent for friction modification. Said further constituent being, for example, boron nitrite and/or Teflon. The percentage of the further friction modification constituent amounts to 15% by weight or less, preferentially 10% by weight or less, further preferentially 5% by weight or less, and should the friction modification constituent be provided in the composite material, at least 0.2% by weight or at least 0.5% by weight or at least 1% by weight relative to the total weight of the composite material.

In a further embodiment according to the first aspect, the invention is characterized by the percentages of the polymeric substrate, the first fibrous reinforcing material and the second reinforcing material together adding up to 97% by weight or more, in particular 100% by weight.

In a second aspect, the invention relates to a mechanical component for force and motion transmissions which comprises a composite material according to at least one embodiment pursuant to the first aspect of the invention. The inventive mechanical component is characterized by low wear. In particular, the mechanical component also exhibits low wear when in contact with ultrapure water.

In one embodiment of the second aspect, the invention relates to a mechanical component, wherein the mechanical component is a gear.

In a third aspect, the invention relates to a gear pump which is characterized by the gear pump having at least one gear in accordance with one embodiment pursuant to the second aspect of the invention. Due to the design, the gears of the gear pump are suspended in the fluid to be pumped. The advantage of the gear pump according to the invention is to be seen in it exhibiting less wear vis-à-vis the pumping of ultrapure water, in particular also at increased temperatures. It was further determined that the gear pump is also low-wear when pumping oxidizing disinfectants, e.g. during heat cleaning of medical devices. The inventive gear pump is therefore suitable for use in the medical technology field and in particular as pumping apparatus in dialysis machines.

EXAMPLES

Block on the Ring Test

The "Block on the Ring Test" was conducted based on the specifications of ASTM G77-17. A test sample measuring 4×4×17 mm was produced from the composite material to be tested. The test sample was mounted in a test bed and set onto an annular body. The annular body consisted of CrNiMo steel. The test body was subsequently subjected to a force of 2.5 MPa and pressed onto the outer surface of the ring. The ring was set into rotation such that the test sample slid over the contact area of the annular body at a relative speed of 0.5 m/s. The test temperature of the ring and test sample was set at 23° C. The test sample and ring were flushed with water during testing. A relative total sliding distance of 36000 m was traversed.

(1) Specific Wear Rate

To determine the specific wear rate, an electrical voltage of 2.5 V was applied between the test sample and annular body. The voltage applied generated a sample and ring surface charge which simulated the corrosive conditions under ultrapure water application of the composite material. Common laboratory demineralized water was used as the lubricant. The amount of test sample abrasive wear resulting during sliding was measured as a function of time. The specific wear coefficient was determined from the gradient of a detected linear progression between abrasive wear amount and time.

At the same time, the friction coefficient was determined via the torque of the driven annular body.

The same process conditions were in each case preset for comparative tests on different composite materials so that the determined specific wear rate and frictional coefficient were only dependent on the composition of the respectively tested composite materials.

Production of the Composite Materials (1) Example 1: PEEK/CF/GF—Composite Material of PEEK Carbon Fiber and Glass Fiber A mass of polyether ether ketone from the Victrex company, carbon fibers having a thermal expansion coefficient of $-0.1 \times 10^{-6}$/K and glass fibers having an electrical conductivity of $1 \times 10^{-9}$ S/m were compounded into a composite material by melt extrusion and processed into a test sample. Carbon fiber and glass fiber were used at the same parts by weight. The percentage of carbon fibers and glass fibers in the test sample in each case amounted to 15% by weight. The specific wear coefficient and friction coefficient were determined via the "Block on the Ring Test." Furthermore, the thermal expansion of the composite material was determined by thermomechanical analysis. The values are shown in table 1.

(2) Example 2: PEEK/CF—Composite Material of PEEK and Carbon Fiber—Comparison Example A mass of polyether ether ketone from the Victrex company and carbon fibers having a thermal expansion coefficient of $-0.1 \times 10^{-6}$/K were compounded by melt extrusion and processed into a test sample. The percentage of carbon fibers in the test sample amounted to 30% by weight. The specific wear coefficient and friction coefficient were determined via the "Block on the Ring Test." Furthermore, the thermal expansion of the composite material was determined by thermomechanical analysis. The values are shown in table 1.

Example 3: PEEK/CF Composite Material of PEEK and Glass Fiber—Comparison Example A mass of polyether ether ketone from the Victrex company and glass fibers having an electrical conductivity of $1\times10^{-9}$ S/m were compounded by melt extrusion and processed into a test sample. The respective percentage of glass fibers in the test sample amounted to 30% by weight. The specific wear coefficient and friction coefficient were determined via the "Block on the Ring Test." Furthermore, the thermal expansion of the composite material was determined by thermomechanical analysis. The values are shown in table 1.

Example 4—Comparison Example

A test sample was produced from PEEK. The specific wear coefficient and friction coefficient were determined via the "Block on the Ring Test." The thermal expansion of the composite material was furthermore determined. The values are shown in table 1.

TABLE 1

| Example | Thermal expansion coefficient $[10^{-6}/K]$ | Friction coefficient $[\mu s]$ | Specific wear rate $[10^{-6} mm^3/Nm]$ |
|---|---|---|---|
| (1) PEEK/CF/GF | 7 | 0.14 | 0.9 |
| (2) PEEK/CF | 4 | 0.14 | 9 |
| (3) PEEK/GF | 16 | 0.22 | 8 |
| (4) PEEK | 47 | 0.17 | 4 |

The results show that the inventive PEEK/CF/GF composite material exhibits a coefficient of friction corresponding to the PEEK/CF composite material.

The friction coefficient is thereby lower than that of the PEEK/CF composite material. The thermal expansion coefficient of PEEK/CF/GF is lower than that of the PEEK/CF composite material, albeit increased relative the PEEK/CF composite material due to the percentage of glass fiber. The specific wear rate of the PEEK/CF/GF composite material was unexpectedly significantly lower than the specific wear rate of the comparison PEEK/CF and PEEK/CF composite materials.

The invention claimed is:

1. A composite material for mechanical components of force and motion transmission comprising at least three constituents:
   (i) at least 45% by weight of a substrate material in relation to the total weight of the composite material,
   (ii) 3 to 20% by weight of a first fibrous reinforcing material in relation to the total weight of the composite material, and
   (iii) 10 to 45% by weight of a second reinforcing material in relation to the total weight of the composite material, wherein
the first fibrous reinforcing material has a lower thermal expansion coefficient than the second reinforcing material and wherein the second reinforcing material has a lower electrical conductivity than the first fibrous reinforcing material and wherein the parts by weight of the constituents contained in the composite material add up to 100%, and wherein the first fibrous reinforcing material exhibits a thermal expansion of from $-0.15\times10^{-6}$/K to $2\times10^{-6}$/K parallel to the direction of the fibers and the second reinforcing material has an electrical conductivity of $10^{-4}$ S/m or less.

2. The composite material according to claim 1, wherein the first fibrous reinforcing material and the second reinforcing material are isotropically dispersed in the substrate material.

3. The composite material according to claim 1, wherein the second reinforcing material is fibrous.

4. The composite material according to claim 1, wherein the substrate material is a polymer selected from the group consisting of polyaryl ether ketone, polyaryl sulfone and polycarbonate.

5. The composite material according to claim 1, wherein the first fibrous reinforcing material contains or is carbon fiber.

6. The composite material according to claim 1, wherein the second reinforcing material contains or is glass fiber.

7. The composite material according to claim 1, wherein the percentage of the first fibrous reinforcing material in the composite material amounts to 3% to 18% by weight relative to the total weight of the composite material.

8. The composite material according to claim 1, wherein the percentage of the second reinforcing material in the composite material amounts to 10% to 40% by weight relative to the total weight of the composite material.

9. The composite material according to claim 1, wherein the percentage of the substrate material in the composite material amounts to at least 50% by weight relative to the total weight of the composite material.

10. The composite material according to claim 1, wherein the weight ratio of the second reinforcing material to the first fibrous reinforcing material amounts to 3:1 to 1:1.

11. The composite material according to claim 1, wherein the composite material comprises an antioxidant.

12. The composite material according to claim 11, wherein the antioxidant is a primary and/or a secondary antioxidant.

13. The composite material according to claim 11, wherein a proportion of the antioxidant in the composite material is 0.001% to 2.5% by weight, based on the total weight of the composite material.

14. The composite material according to claim 1, wherein fibers of the first fibrous reinforcing material and/or fibers of the second reinforcing material have a fiber diameter of from 11 μm to 10 μm.

15. The composite material according to claim 1, wherein fibers of the first fibrous reinforcing material and/or fibers of the second reinforcing material have a length of 10 μm to 60 μm.

16. The composite material according to claim 1, wherein a ratio of diameter to length for the fibers of the first fibrous reinforcing material and fibers of the second reinforcing material is greater than 1:2 to 1:20.

17. The composite material according to claim 1, wherein percentages of the substrate material, the first fibrous reinforcing material and the second reinforcing material together add up to 100% by weight.

18. A mechanical component for force and motion transmissions comprising the composite material according to claim 1.

19. The mechanical component according to claim 18, wherein said mechanical component is a gear.

20. A gear pump comprising at least one of said gear according to claim 19.

21. A method for conducting medical pumping of a liquid, said method comprising utilizing at least one of said mechanical component of claim 18 that is suspended in said liquid.

22. The method of claim 21, wherein said medical pumping comprises dialysis pumps or pumps for pumping ultra-pure water.

\* \* \* \* \*